(12) United States Patent
Rollins

(10) Patent No.: US 9,700,375 B2
(45) Date of Patent: Jul. 11, 2017

(54) LASER NIL LIPOSUCTION SYSTEM AND METHOD

(71) Applicant: Rollins Enterprises, LLC, Woodland Hills, CA (US)

(72) Inventor: Aaron J. Rollins, Los Angeles, CA (US)

(73) Assignee: ROLLINS ENTERPRISES, LLC, Woodland Hills, CA (US)

(*) Notice: Subject to any disclaimer, the term of this patent is extended or adjusted under 35 U.S.C. 154(b) by 79 days.

(21) Appl. No.: 13/924,641

(22) Filed: Jun. 24, 2013

(65) Prior Publication Data

US 2014/0005637 A1  Jan. 2, 2014

Related U.S. Application Data

(60) Provisional application No. 61/666,853, filed on Jun. 30, 2012.

(51) Int. Cl.
| | |
|---|---|
| *A61M 1/00* | (2006.01) |
| *A61M 19/00* | (2006.01) |
| *A61B 18/22* | (2006.01) |
| *A61B 17/34* | (2006.01) |
| *A61M 25/01* | (2006.01) |
| *A61B 18/00* | (2006.01) |
| *A61B 18/20* | (2006.01) |

(52) U.S. Cl.
CPC .............. *A61B 18/22* (2013.01); *A61M 1/008* (2013.01); *A61B 2018/00464* (2013.01); *A61B 2018/2005* (2013.01); *A61M 1/0039* (2013.01); *A61M 1/0064* (2013.01); *A61M 19/00* (2013.01); *A61M 2202/0014* (2013.01); *A61M 2202/08* (2013.01)

(58) Field of Classification Search
CPC .......... A61B 18/22; A61B 2018/00464; A61B 2018/2005; A61B 2017/00238; A61B 2017/00292; A61B 2217/005; A61M 1/008; A61M 19/00; A61M 2202/08; A61M 2202/09; A61M 1/0039; A61M 1/0058; A61M 1/0064; A61M 1/0082; A61M 1/0084; A61M 1/0086; B05B 3/02; B05B 3/008
See application file for complete search history.

(56) References Cited

U.S. PATENT DOCUMENTS

| 2,439,262 A | * | 4/1948 | Gresham et al. ............... 62/414 |
| 4,447,225 A | * | 5/1984 | Taff et al. ...................... 604/71 |
| 5,304,128 A | * | 4/1994 | Haber ................. A61M 5/2046 604/143 |

(Continued)

*Primary Examiner* — Adam Marcetich
(74) *Attorney, Agent, or Firm* — McDermott Will & Emery LLP

(57) ABSTRACT

A minimally invasive fat cell removal system and method is provided using a numbing component, a laser component, and a NIL component. A cannula and fiber of the laser component are insertable into a body of a patient at a biopsy punch to liquefy a fat cell via a tumescent fluid and/or a laser. A NIL cannula of the NIL component is insertable into the body to remove the fat cell via suction and/or nutation. An anesthetic device of the numbing component may reduce sensation of the body where the cannula is insertable. The fat cell may be harvested and implanted at another location of the body.

17 Claims, 6 Drawing Sheets

(56) References Cited

U.S. PATENT DOCUMENTS

| | | | | |
|---|---|---|---|---|
| 6,336,925 B1* | 1/2002 | Malak | A61M 1/008 604/22 |
| 6,375,648 B1* | 4/2002 | Edelman | A61M 3/0279 604/265 |
| 2003/0167053 A1* | 9/2003 | Taufig | A61M 1/0084 604/542 |
| 2003/0187383 A1* | 10/2003 | Weber | A61B 17/32002 604/22 |
| 2005/0123484 A1* | 6/2005 | Hirsh et al. | 424/45 |
| 2006/0224148 A1* | 10/2006 | Cho et al. | 606/15 |
| 2007/0052139 A1* | 3/2007 | Gilbert | 264/400 |
| 2007/0213688 A1* | 9/2007 | Klein | A61M 5/158 604/523 |
| 2008/0188835 A1* | 8/2008 | Hennings | A61B 18/22 604/542 |
| 2009/0182315 A1* | 7/2009 | Zigan | A61B 18/22 606/15 |
| 2010/0094267 A1* | 4/2010 | Ference et al. | 606/15 |
| 2011/0034905 A1* | 2/2011 | Cucin | 604/542 |
| 2011/0129375 A1* | 6/2011 | Kotsonis | 418/4 |
| 2011/0130749 A1* | 6/2011 | Arcus Villacampa | A61B 18/22 606/15 |
| 2011/0166502 A1* | 7/2011 | Nallakrishnan | A61F 9/00745 604/22 |
| 2011/0172652 A1* | 7/2011 | Neuberger | 606/15 |
| 2011/0264083 A1* | 10/2011 | Welches | A61B 18/201 606/14 |
| 2011/0307001 A1* | 12/2011 | Becker | 606/192 |
| 2012/0165725 A1* | 6/2012 | Chomas | A61M 1/008 604/22 |
| 2012/0322783 A1* | 12/2012 | Klein | A61M 5/14 514/206 |
| 2013/0006225 A1* | 1/2013 | Cucin | 604/542 |
| 2015/0209565 A1* | 7/2015 | Dauvister | A61M 1/0039 604/22 |

* cited by examiner

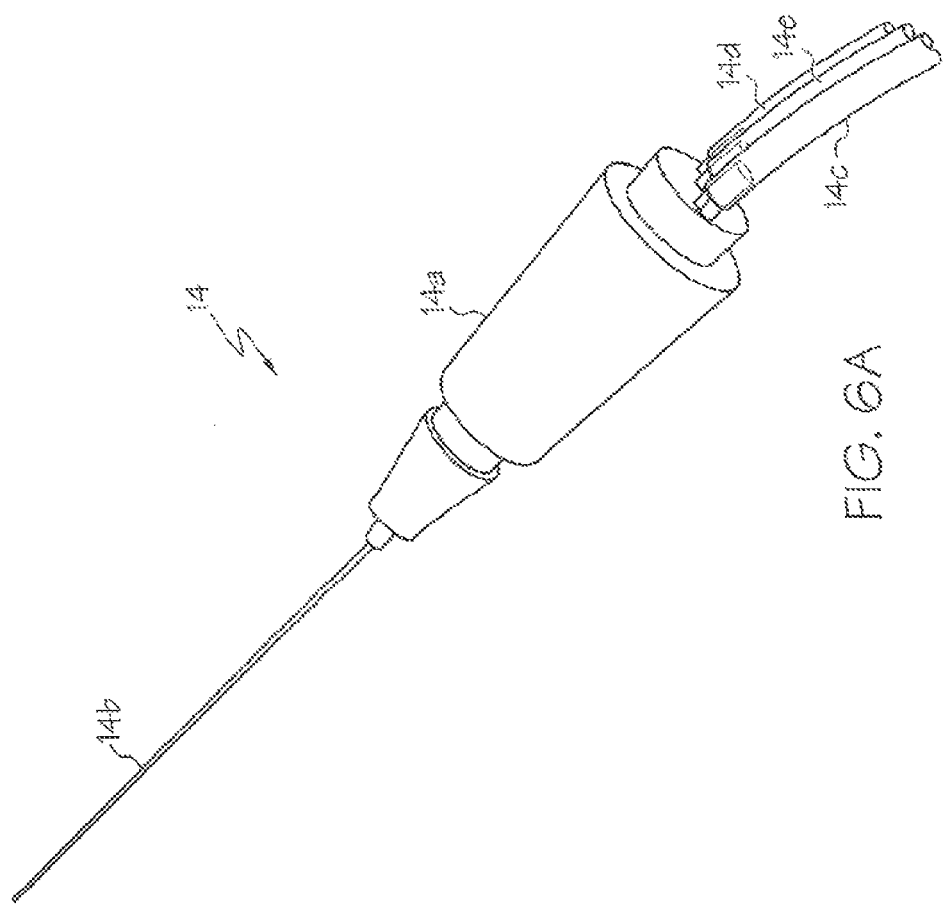

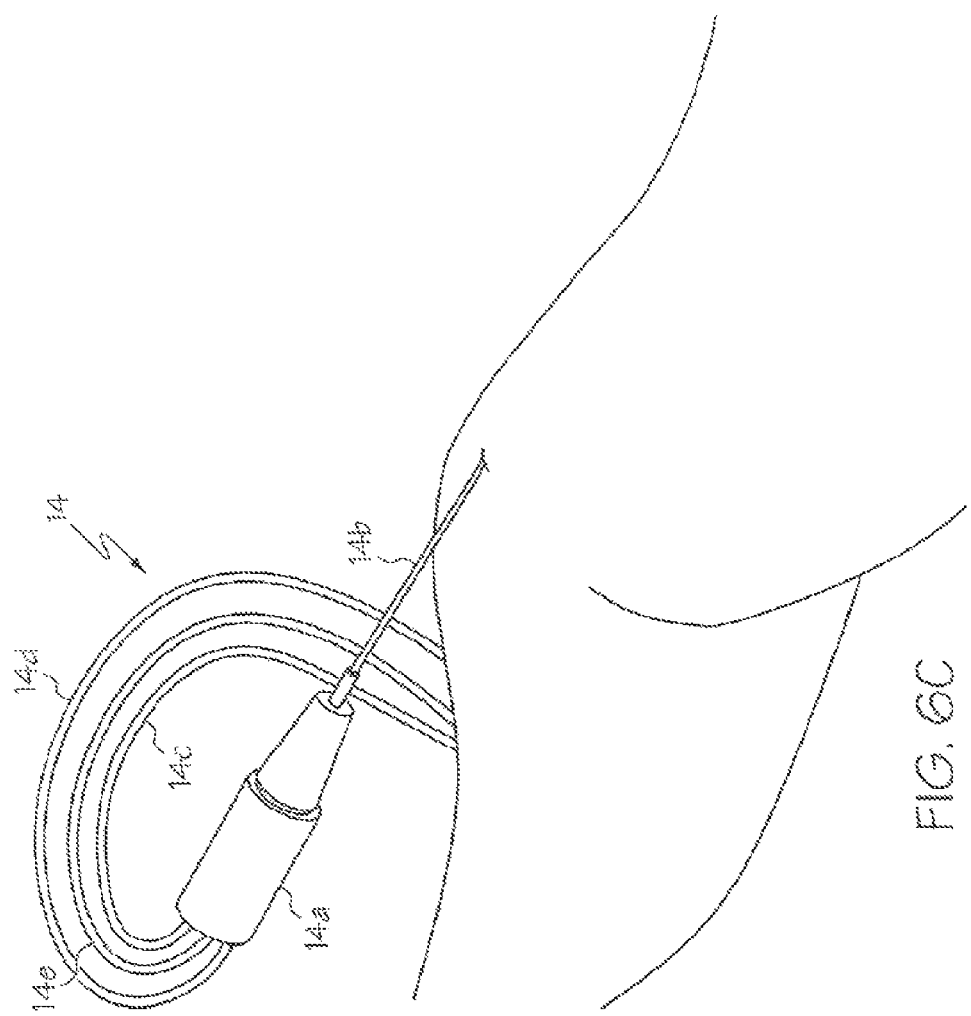

LASER NIL LIPOSUCTION SYSTEM AND METHOD

CROSS-REFERENCE TO RELATED APPLICATIONS

This non-provisional application claims priority of U.S. Provisional Patent Application No. 61/666,853 filed on Jun. 30, 2012, which is incorporated herein by reference in its entirety.

FIELD OF THE INVENTION

The invention relates to surgical procedures. More particularly, the invention relates to liposuction surgical procedures.

BACKGROUND

Liposuction is a cosmetic surgery operation that removes fat form a site within a body. Typically, liposuction may be performed to remove fat from the abdomen, thighs, buttocks, neck, back, arms, and other parts of the body. Early liposuction procedures used curettage techniques, which involved scraping or scooping the fat from within the body. These techniques were abrasive and often involved health risks.

Due to the high risks involved with curettage, liposuction techniques evolved to use a suction-assisted removal after infusing a liquid into tissue. However, this method achieved only mixed results and raised concerns over effects caused to the body from the introduction of a high volume of fluid. Also, concerns arose regarding potential toxicity of these fluids when introduced into the body at high volume.

To cope with these concerns, physicians began using ultrasonic techniques to liquefy fat for removal. These techniques involved focusing ultrasonic energy at the fat, causing it to become a liquid that could be removed. However, due to an increased report of complications, such ultrasonic methods have also raised concerns. Additional techniques have been created using nutational infrasonic liposculpture (NIL) systems, which uses infrasonic vibration to remove fat.

In new liposuction surgical procedures, physicians have begun using lasers to liquefy fat for removal. However, such laser based procedures are underdeveloped, and produce mixed results. Additionally, using lasers with currently known liposuction procedures may not allow a physician to remove fat with high efficiency. What is needed is liposuction technique to remove fat from within a person using a method with high efficiency and effectiveness. What is also needed is a liposuction procedure that is minimally invasive and causes little to no pain.

SUMMARY

According to embodiments of the present invention, a laser NIL liposuction system and method is described that may remove fat from within a human using at least laser and NIL based nutation. The laser NIL liposuction technique, according to an embodiment of the present invention, may remove fat from within a person using a method with high efficiency and effectiveness. The laser NIL liposuction method of the present invention also provides a procedure that is minimally invasive and causes little to no pain.

The present invention advantageously allows a patient to reduce the volume of fat in his or her body using a relatively painless technique that produces results. Through practice of the various embodiments of the present invention, fat may be gently removed using a method that improves on a number of fat removal techniques without requiring general anesthesia. Due to the minimally invasive nature of the methods and system, according to the embodiments of the present invention disclosed herein, a number of patients may experience an accelerated recovery and a decreased amount of downtime required for the body to heal.

Another advantage of the systems and methods described herein is that the incision created by the biopsy punch through which the laser component and NIL component are inserted, in combination with the anesthetic component that does not use a needle, does not require stitches so that the method produces a naturally healing, scarless wound at the incision.

Still another advantage of the systems and methods described herein is that they produce a high quality fat that does not contain debris, which can be transferred to other areas of the body for use in other medical procedures such as, for example, cosmetic surgical procedures.

A method is provided by the present invention that improves over the fat removal techniques of the prior art. The method may include driving a numbing solution into a patient using a jet injector, eliminating the need for a needle. The method also advantageously provides access to the interior of a patient by using a biopsy punch, for example, a two millimeter biopsy punch, eliminating the need for a scalpel. Due at least to these advantages, the method improves over the prior art by conditioning a patient for efficient fat removal while eliminating the need for placement of stiches or other sutures.

The method provided by the present invention additionally improves over the prior art by numbing a patient using a cannula, such as a blunt 18 gauge cannula. The method also advantageously assists fat removal by applying a laser of 10 watts or higher to condition the fat. Using the method of the present invention, the fat may be removed using cannulae from between 2 mm-4.5 mm that utilizes a powered infrasonic nutational system. The method of the present invention increases efficiency of fat removal from a patient while reducing the pain and recovery times caused by fat removal procedures of the prior art.

According to an embodiment of the present invention, a minimally invasive fat cell removal system is provided with a laser component and a NIL component. The laser component may condition a fat cell for removal. The laser component may include a cannula and a fiber to transmit a laser. The NIL component may remove the fat cell. Skilled artisans will appreciate recitation of a fat cell throughout this disclosure to mean one or more fat cell, without limitation. The NIL component may include a NIL cannula and a suction. The cannula and the fiber of the laser component may be inserted into a body of a patient at a biopsy punch. The laser may be transmitted by the fiber to heat the fat cell. Heating the fat cell may induce at least partial liquefaction of the fat cell. The NIL cannula of the NIL component may also be inserted into the body of the patient at the biopsy punch. The fat cell that is at least partially liquefied is removable from the body via the NIL cannula.

In another aspect, the fat cell removal system may include an anesthetic device to provide reduced sensation of the body at a location, the anesthetic device including a numbing component. The cannula may be inserted at the location with reduced sensation. The anesthetic device may provide the reduced sensation via jet injection.

In another aspect, the fiber may be at least partially enclosed by the cannula. The fiber may be insertable into the body via the cannula.

In another aspect, a tumescent fluid may be injectable via the cannula of the laser component to cause the fat cell that will be removed to become tumescent. Injection of the tumescent fluid may facilitate the at least partial liquefaction of the fat cell.

In another aspect, the laser may be emitted at approximately 10 watts or more.

In another aspect, the NIL component may provide nutational movement to the NIL cannula during removal of the fat cell.

In another aspect, the NIL component may include an output through which the fat cell is harvestable. The fat cell that is harvested from the body from a first location may be implantable into the body at a second location to increase a volume of fat cells near or adjacent to the second location.

In another aspect, a stem cell may be implantable with the fat cell at the second location to increase a likelihood of acceptance of the fat cell by the body at the second location.

According to an embodiment of the present invention, a method aspect is provided for removing a fat cell. The method may include (a) using a laser component to condition the fat cell for removal. Step (a) may further include (i) positioning a fiber at least partially in a cannula, (ii) inserting the cannula with the fiber into a body of a patient at a biopsy punch, and (iii) operating a laser to be transmitted via the fiber to heat the fat cell to induce an at least partial liquefaction of the fat cell. The method aspect may additionally include (b) using a NIL component to remove the fat cell. Step (b) may further include (iv) inserting a NIL cannula into the body of the patient at the biopsy punch, and (v) extracting the fat cell via suction through the NIL cannula. Removal of the fat cell is minimally invasive.

In another aspect of the method, before step (a), an additional step may be included for (c) using a numbing component to reduce sensation of the body at a location using an anesthetic device. The cannula may be insertable at the location. The anesthetic device may operate via jet injection.

In another aspect of the method, before step (iii), the method may further include (vi) injecting a tumescent fluid via the cannula of the laser component to cause the fat cell that will be removed to become tumescent and facilitate the at least partial liquefaction of the fat cell.

In another aspect of the method, the laser may be emitted at approximately 10 watts or more.

In another aspect of the method, the NIL component may provide nutational movement to the NIL cannula during removal of the fat cell.

In another aspect of the method, the NIL component may include an output through which the fat cell is harvestable. Step (b) may further include (d) harvesting the fat cell from a first location using the output.

In another aspect of the method, after step (d), an additional step may be included for (e) implanting the fat cell that is harvested into the body at a second location to increase a volume of fat cells adjacent to the second location.

In another aspect of the method, step (e) may further include implanting a stem cell with the fat cell at the second location to increase a likelihood of acceptance of the fat cell by the body at the second location.

According to an embodiment of the present invention, a method aspect is provided for removing a fat cell that is minimally invasive. The method may include (a) using a numbing component to reduce sensation of a body of a patient at a first location using an anesthetic device. The method may also include (b) using a laser component to condition the fat cell for removal. Step (b) may further include (i) positioning a fiber at least partially in a cannula, (ii) inserting the cannula with the fiber into the body of the patient at the first location, (iii) injecting a tumescent fluid via the cannula to cause the fat cell that will be removed to become tumescent, and (iv) operating a laser to be transmitted via the fiber to heat the fat cell to induce an at least partial liquefaction of the fat cell. The fat cell that has become tumescent may facilitate the at least partial liquefaction of the fat cell. The method may additionally include (c) using a NIL component to remove the fat cell. Step (c) may further include (v) inserting a NIL cannula into the body of the patient at the first location, and (vi) extracting the fat cell by suction through the NIL cannula, the fat cell being harvestable from the first location.

In another aspect of the method, the anesthetic device may operate via jet injection.

In another aspect of the method, step (a) further may further include creating a biopsy punch at the first location to create an incision through and into which the laser component and NIL component are insertable.

In another aspect of the method, the incision created by the biopsy punch does not require stitches so that the method produces a naturally healing, scarless wound at the incision.

In another aspect of the method, the NIL component may provide nutational movement to the NIL cannula during removal of the fat cell.

In another aspect of the method, the NIL component may include an output through which the fat cell is harvestable. After step (c), the method may further include (d) harvesting the fat cell from the first location using the output.

In another aspect of the method, after step (d), an additional step may be included for (e) implanting the fat cell that is harvested into the body at a second location to increase a volume of fat cells adjacent to the second location.

In another aspect of the method, step (e) may further include implanting a stem cell with the fat cell at the second location to increase a likelihood of acceptance of the fat cell by the body at the second location.

Unless otherwise defined, all technical terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents and other references mentioned herein are incorporated by reference in their entirety. In the case of conflict, the present specification, including definitions will control.

BRIEF DESCRIPTION OF THE DRAWINGS

FIG. 6A is a perspective view of a NIL component.

FIG. 6B is a perspective view of a NIL cannula of the NIL component of FIG. 6A.

FIG. 6C is a perspective view of the NIL component of FIG. 6A in use with a method as described herein.

DETAILED DESCRIPTION

Figure 1:
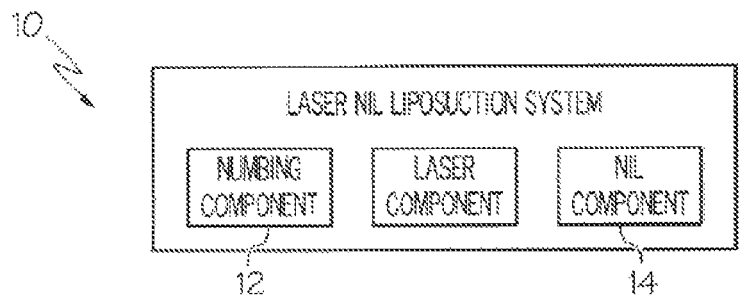
FIG. 1 is a block diagram of a laser NIL liposuction system, according to an embodiment of the present invention

The present invention is best understood by reference to the detailed drawings and description set forth herein. Embodiments of the invention are discussed below with reference to the drawings; however, those skilled in the art will readily appreciate that the detailed description given herein with respect to these figures is for explanatory purposes as the invention extends beyond these limited embodiments. For example, in light of the teachings of the present invention, those skilled in the art will recognize a multiplicity of alternate and suitable approaches, depending upon the needs of the particular application, to implement the functionality of any given detail described herein beyond the particular implementation choices in the following embodiments described and shown. That is, numerous modifications and variations of the invention may exist that are too numerous to be listed but that all fit within the scope of the invention. Also, singular words should be read as plural and vice versa and masculine as feminine and vice versa, where appropriate, and alternative embodiments do not necessarily imply that the two are mutually exclusive.

The present invention should not be limited to the particular methodology, compounds, materials, manufacturing techniques, uses, and applications, described herein, as these may vary. The terminology used herein is used for the purpose of describing particular embodiments only, and is not intended to limit the scope of the present invention. As used herein and in the appended claims, the singular forms "a," "an," and "the" include the plural reference unless the context clearly dictates otherwise. Thus, for example, a reference to "an element" is a reference to one or more elements and includes equivalents thereof known to those skilled in the art. Similarly, for another example, a reference to "a step" or "a means" may be a reference to one or more steps or means and may include sub-steps and subservient means.

All conjunctions used herein are to be understood in the most inclusive sense possible. Thus, a group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should be read as "and/or" unless expressly stated otherwise. Structures described herein are to be understood also to refer to functional equivalents of such structures. Language that may be construed to express approximation should be so understood unless the context clearly dictates otherwise.

Unless otherwise defined, all terms (including technical and scientific terms) are to be given their ordinary and customary meaning to a person of ordinary skill in the art, and are not to be limited to a special or customized meaning unless expressly so defined herein.

Terms and phrases used in this application, and variations thereof, especially in the appended claims, unless otherwise expressly stated, should be construed as open ended as opposed to limiting. As examples of the foregoing, the term "including" should be read to mean "including, without limitation," "including but not limited to," or the like; the term "having" should be interpreted as "having at least"; the term "includes" should be interpreted as "includes but is not limited to"; the term "example" is used to provide exemplary instances of the item in discussion, not an exhaustive or limiting list thereof; and use of terms like "preferably," "preferred," "desired," "desirable," or "exemplary" and words of similar meaning should not be understood as implying that certain features are critical, essential, or even important to the structure or function of the invention, but instead as merely intended to highlight alternative or additional features that may or may not be utilized in a particular embodiment of the invention.

Those skilled in the art will also understand that if a specific number of an introduced claim recitation is intended, such an intent will be explicitly recited in the claim, and in the absence of such recitation no such intent is present. For example, as an aid to understanding, the appended claims may contain usage of the introductory phrases "at least one" and "one or more" to introduce claim recitations; however, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C" is used, in general, such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.).

All numbers expressing dimensions, quantities of ingredients, reaction conditions, and so forth used in the specification are to be understood as being modified in all instances by the term "about" unless expressly stated otherwise. Accordingly, unless indicated to the contrary, the numerical parameters set forth herein are approximations that may vary depending upon the desired properties sought to be obtained.

The present invention will now be described in detail with reference to embodiments thereof as illustrated in the accompanying drawings. In the following description, a laser NIL liposuction system and method will be discussed. Those of skill in the art will appreciate alternative labeling of the laser NIL liposuction method as a liposuction method, procedure, operation, technique, other similar names, or generally the invention. Skilled readers should not view the inclusion of any alternative labels as limiting in any way.

Additionally, the laser NIL liposuction method may be performed using a laser NIL liposuction system. At least one embodiment of the laser NIL liposuction systems will be described throughout this disclosure. Those of skill in the art will appreciate alternative labeling of the laser NIL liposuction system as a liposuction system, apparatus, device, or other similar term. As with the method, skilled readers should not view the inclusion of any alternative labels as limiting in any way.

According to the various embodiments of the present invention, a medical procedure may be performed using the system disclosed herein to reduce the volume of fat in the body of a patient. The procedure may be performed using no needle or scalpel. As a result, the procedure may also not require stiches or removal of the same. Additionally, the procedure may advantageously be performed without requiring the use of general anesthesia, eliminating the risks involved with its use. Furthermore, the fat may be harvested with minimal debris and used for transfer to other parts of a patient's body.

Fat removal using the system and method of the present invention may be less invasive than standard liposuction and therefore there is less downtime and faster results. Whereas typical liposuction takes about 6 months to heal, the present invention may provide results in about a month in some situations. Being less invasive also means less pain after performance of the procedure. Many patients of the procedure, performed in accordance with the system and methods of the present invention, can be back at work sooner than with traditional fat removal methods of the prior art.

Referring now to FIG. 1, a laser NIL liposuction system 10, according to an embodiment of the present invention, will now be discussed. Additionally, a method of using a laser NIL liposuction system will be discussed. As shown in FIGS. 3, 5A, 5B, 6A, and 6B, the laser NIL liposuction system 10 may include a numbing component 12, a laser component, and a NIL component 14. Additional components may also be included in the system, which will be discussed below. One or more element of the invention may be used or shared by one or more component of the system, without limitation.

The laser component will now be discussed in more detail. The laser component may include a cannula with a fiber. The fiber may transmit or carry a laser. In one embodiment, the fiber may be an optical fiber. The cannula may be a thin tube through which the fiber may be passed. In one embodiment, the cannula may be a NIL cannula. The cannula may assist with keeping the laser fiber stiff so that the laser may be inserted into the body of the patient. In one example, the cannula may be an 18 gauge garden spray cannula having holes located about its sides.

The fiber may transmit laser energy, or focused and energized light. In one embodiment, the laser may be passed through the fiber with a power of approximately ten watts. In another embodiment, the laser is powered with greater than 10 watts. For example, the laser may be powered with 10, 11, 12, 13, 14, 15, 18, 20, 25, 30, 35, 40, 45, 50, 60, 70, 80, 90, or other wattages. The laser energy may be emitted from an end of the fiber, for example, an end of the fiber that has been inserted into a patient using the cannula, to heat surrounding tissue. Use of the laser component will be discussed in more detail below.

The NIL component 14 will now be discussed in more detail. The nutational infrasonic liposculpture (NIL) system generally includes at least a source of nutational motion 14a, a NIL cannula 14b, and source of suction. In at least one embodiment, the cannula of the laser component and the NIL component 14 may be one shared cannula 14b.

Nutation may be defined as a rocking, swaying, or nodding motion in an axis or rotation. The source of nutational motion may include a motor, pneumatic device, or other source of rotating and/or oscillating motion. In an example, and without limitation, a nutating motion can be created by a configuration including a swash plate with an attached shaft configured to interact with a fixed plate. The fixed plate may include one or more skewed bearings. As the swash plate is carried on the fixed plate, the shaft attached to the swash plate may be moved with a nutating motion. The shaft may be a cannula, such as the NIL cannula.

A source of suction may be included by or operatively connected to the NIL component 14. More specifically, according to at least one embodiment, the source of suction may be connected in the NIL component 14 to create suction in a NIL cannula 14b. Fat may be drawn through the NIL cannula 14b, due in part to the suction, with the received fat being expelled through a shared or dedicated output. In one embodiment, such as the one shown in FIGS. 6A and 6C, the NIL component 14 may have a suction input 14c and suction output 14d through which suction is provided to the NIL component. In this embodiment, the NIL component 14 may include an additional output 14e, by which fat drawn through the NIL cannula 14b may be removed from the system and optionally harvested. By using the system of the present invention, the harvested fat may be high quality fat, having minimal debris and capable of being transferred to other areas of the body. Those of skill in the art will appreciate additional embodiments of the NIL component, which are intended to be included within the scope of this disclosure.

Figure 3:
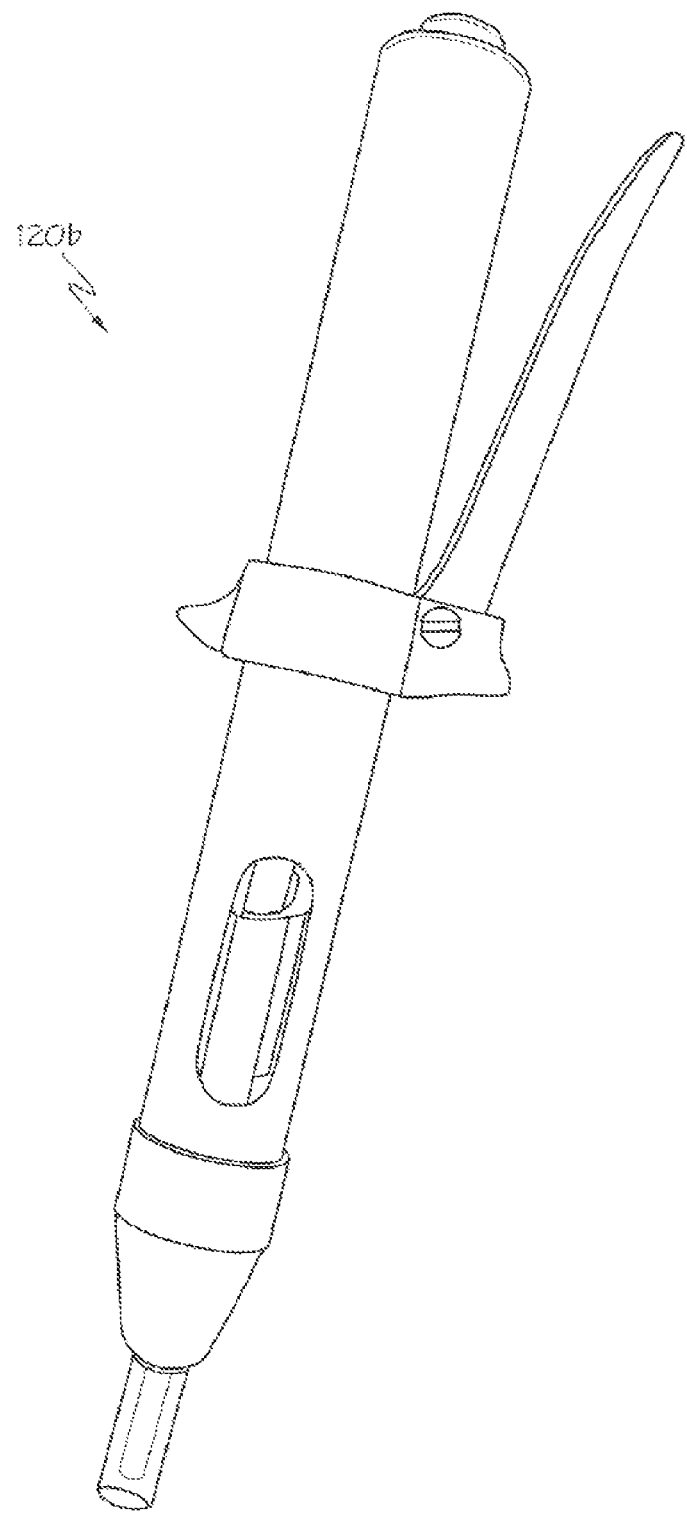
FIG. 3 is a perspective view of one embodiment of a numbing component that is a jet injector.
Figure 4:
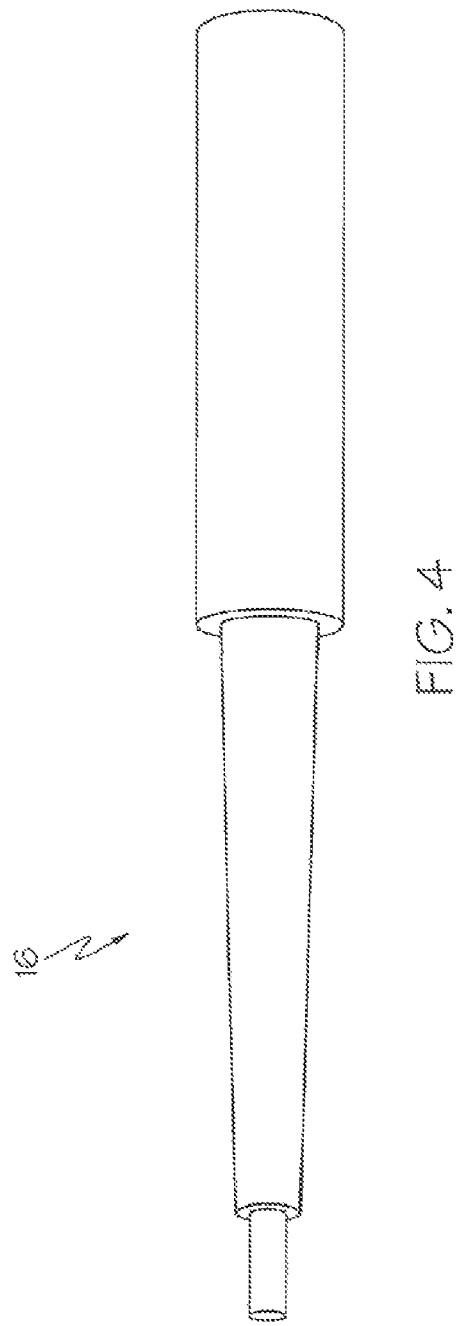
FIG. 4 is a side view of a biopsy punch.
Figure 5A:
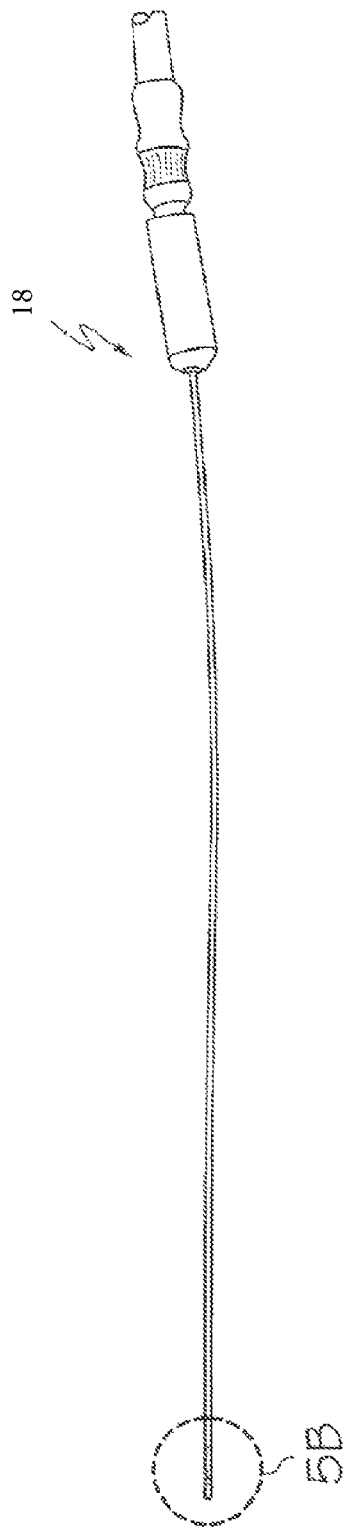
FIG. 5A is a side view of another embodiment of a cannula that is a garden spray blunt tumescent cannula.
Figure 5B:
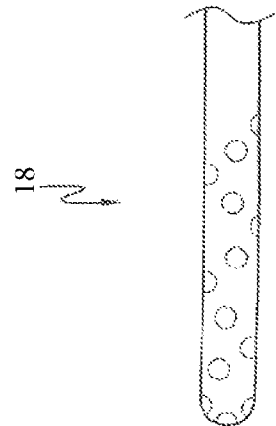
FIG. 5B is a close-up view of one end of the cannula of FIG. 5A.

The numbing component 12 will now be discussed in greater detail. The numbing component may include an anesthetic device 120b as shown in FIG. 3 and may use a biopsy punch 16 such as the one shown in FIG. 4. The anesthetic device may be used to reduce sensation in a localized area where the laser component and/or NIL component may enter the body of the patient. By using a localized numbing process, fat removal may be performed while a patient is in an awakened state. The anesthetic device of the numbing component may be a jet injector 120a as shown in FIG. 3, which may propel an anesthetic into the skin of a patient using a high pressure stream of air injected into the pores of the patient's skin. This propelled substance may be received by the subcutaneous tissue. The jet injector may inject a substance into the skin of a patient without the insertion of a needle, resulting in reduced pain for the patient. Application of the anesthetic by jet injection is advantageous over being received by needle injection, because a substance introduced into the skin using a jet injection may be more quickly dispersed throughout a localized area of the body and will not need to be diffused from an initial pool-like area caused by local needle injection.

The anesthetic may be a local anesthetic, such as lidocaine. The anesthetic may also include epinephrine, which may affect operation of the nerves around the area receiving the anesthetic. Additionally, epinephrine may be included with lidocaine to prolong the action of the anesthetic and affect the perception of pain by the nervous system of the patient. Additionally, nitrous oxide may be provided to a patient to calm his or her nerves during a procedure. Nitrous oxide may be provided to supplement or substitute administration of other anesthetics.

In operation, the laser NIL liposuction system may use the laser and NIL components to effectively and efficiently remove undesired fat from a body. Through the use of both laser and NIL in the liposuction method illustrated below, the present invention may advantageously provide liposuction surgical procedures to patients that are minimally invasive and produce significant results.

Figure 2:
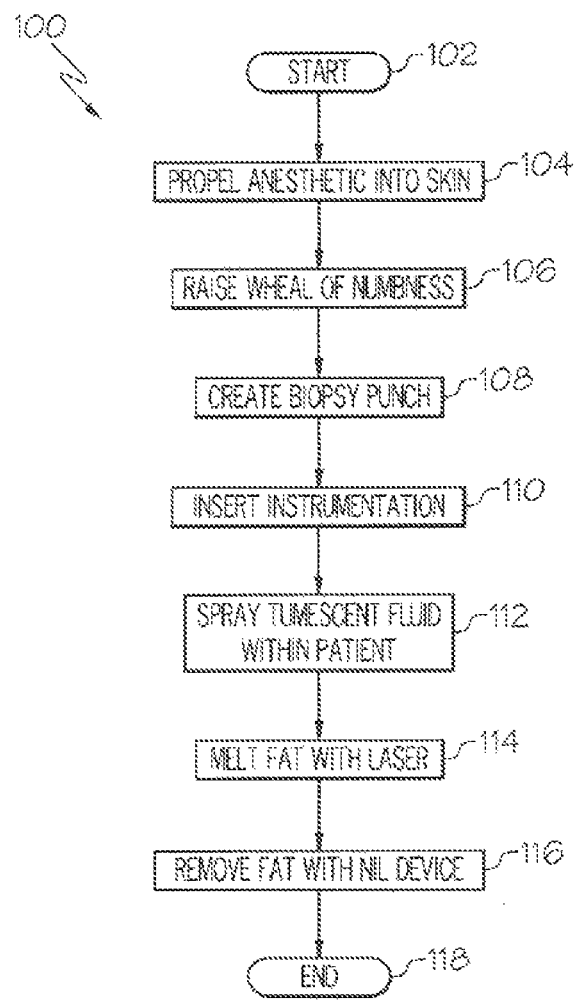
FIG. 2 is flow chart describe a laser NIL liposuction method, according to an embodiment of the present invention.

Referring now to flowchart 100 of FIG. 2, an illustrative laser NIL liposuction method will now be discussed. This illustrative laser NIL liposuction method may be performed using a laser NIL liposuction system. An example of a laser NIL liposuction system has been discussed throughout this disclosure. Those of skill in the art will appreciate that the example method illustrated in flowchart 100 is provided to clearly illustrate an embodiment of the present invention. Skilled artisans, after having the benefit of this disclosure, will appreciate additional embodiments that would be considered within the scope and spirit of the present invention, and which are intended to be included by this disclosure.

The method illustrated by flowchart 100 may be performed while a patient is in an awakened state. More specifically, the method of flowchart 100 may be performed without requiring the patient be sedated with a general anesthesia or other form of sedation. Starting at Block 102, an anesthetic may be propelled or otherwise introduced into the skin (Block 104). As discussed above, the anesthetic may be a local anesthetic, such as lidocaine and/or epinephrine. Preferably, the anesthetic is provided to the patient using a jet injector.

The anesthetic may raise a wheal of numbness around the area through which it is dispersed (Block 106). A biopsy punch may then be created, through which instrumentation may enter the body of the patient (Block 108). For example, a biopsy punch of two millimeters may be created to accommodate instrumentation of similar size. By utilizing a small biopsy punch, the resulting incision may be left open to heal naturally with zero or a negligible amount of scarring, advantageously not requiring stiches or other surgical suture. In other examples, a biopsy punch may be created that is 0.1, 0.2, 0.5, 1, 1.5, 2, 2.5, 3, 3.5, 4, 5, 6, 7, 8, 9, 10, 11, 12, 13, 14, 15, 16, 18, or 20 mm. A person of skill in the art will appreciate the biopsy punch may be created with yet other alternative sizes, which may accommodate for instrumentation that may be used.

Instrumentation may be inserted into the biopsy punch (Block 110). For example, a blunt tumescent cannula may be inserted into the biopsy punch. The cannula, or other instrumentation, may be configured with a size respective to the fat that may be removed. In a specific example, provided without limitation, the cannula may be an 18-gauge garden spray blunt tumescent cannula 18 (such as the one shown in FIGS. 5A and 5B) through which a fluid may be passed. In other examples, the cannula may be 7, 8, 9, 10, 11, 12, 13, 14, 15, 16, 17, 18, 19, 20, 21, 22, 22s, 23, 24, 25, 26, 26s, 27, 28, 29, 30, 31, 32, 33, or 34 gauge, as will be appreciated by a person of skill in the art.

A tumescent fluid may then be sprayed within the patient (Block 112). More specifically, without limitation, the tumescent fluid may be sprayed within, or adjacent to, the fat cell of the patient near to the area from which fat may be removed. The tumescent fluid may be sprayed into the patient using an HK surgical tumescent pump, which will be appreciated by those skilled in the art. The tumescent fluid may cause a tissue, for example fatty tissue, to become tumescent. Preferably, the tissue may become evenly tumescent, and may become somewhat turgid and pale in color.

A laser may then be used to melt the fat around the area from which it may be removed (Block 114). The laser may be inserted through the biopsy punch with the cannula, which may assist in keeping the laser fiber stiff as the laser is inserted into the body. More specifically, without limitation, fibers from the laser component may contact the fat cells, heating the cells via a laser. The heat may cause the cell membranes to swell, causing the fat cells to burst into fatty oil. Additionally, the laser may cause a tightening of the skin around the point of application. This tightening may increase the effectiveness of the liposuction procedure. More specifically, the laser may trigger the production of collagen, which increases the strength and elasticity of the skin interacting with the laser. The laser may also provide additional hemostasis, which helps prevent or decrease undesired bleeding during the procedure.

After the laser has been applied, the NIL component may be used to remove the fat cells from the patient (Block 116). The NIL component may be, for example, an embodiment previously discussed in this disclosure. In one embodiment, a fourth generation NIL component may be used. Additionally, the NIL component may include cannulae with diameters ranging from 2.7 to 4.0 millimeter. In additional embodiments, cannulae may include diameters of about 0.2, 0.5, 0.7, 1, 1.2, 1.5, 1.7, 2, 2.2, 2.5, 2.7, 3, 3.2, 3.5, 3.7, 4, 4.2, 4.5, 5, 5.5, 6, 6.5, 7, or 8 millimeters. The cannulae may be inserted into the biopsy punch previously created, which has been discussed along with Block 108.

The NIL cannulae included in the NIL component may be manipulated using nutation, which may increase efficiency of fat removal from the patient. Through the combination of nutational movement and suction, the NIL component may efficiently and effectively remove the fat from the patient that has been made tumescent and melted by the steps above. Once the fat has been removed from the patient, the operation may terminate at Block 118.

Through the unique and novel use of tumescent fluid, laser, and nutational fat cell manipulation techniques, the present invention may advantageously manipulate and remove fat from a patient with increased efficiency, comfort, and desired results. Additionally, through the methods described above, fat cells may be manipulated and removed from a patient using a minimally invasive procedure that reduce pain levels experienced by many patients.

The present invention improves over the prior art by providing fat removal of a patient that can remain awake during the procedure. Additionally, patients may experience less swelling, less bruising, less discomfort, faster recovery, and less downtime. Furthermore, because of the gentle nature of fat removal, there is quality fat that can be used for transfer in auxiliary procedures such as Brazilian Butt Lift, natural breast augmentation, and injections in the hands to reduce the appearance of aging.

In an embodiment of the present invention, the fat cells extracted via the methods discussed above may be harvested. The harvested fat may be high quality, having minimal or no debris content. Fat cells that have been harvested may be transferred to a different location of a patient's body. For example, fat cells may be removed from a first location of the body using the laser NIL liposuction system, via a method discussed above, and harvested. These harvested fat cells can then be transferred or implanted in a second location of the body. As a specific example, provided without limitation, fat cells may be removed from the waist and abdominal locations of a patient. These fat cells could then be transferred to the breast location of the patient, providing a natural breast augmentation while advantageously using the patient's own tissue and not requiring the introduction of foreign objects or substances into the patient's body.

To increase a likelihood of acceptance for of the transferred fat cells by the body, one or more stem cell may be transferred and/or implanted along with the fat cell. Stem cells are biological cells that can divide and differentiate into various cell types. Stem cells included with the transferred fat cells may act as progenitor cells and increase the likelihood that the body accepts a transferred fat cell. Fat cells that are accepted by the body may be anchored to the new location with assistance of the stem cells. Skilled artisans will appreciate stem cells and biological details relating to the same.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A minimally invasive fat cell removal system comprising:
   a jet injector for propelling an anesthetic into a body of a patient at a location;
   a biopsy punch configured to create one biopsy punch opening in the skin of the patient at the location;
   a laser component comprising a fiber to transmit a laser, the fiber configured to be insertable into the body of the patient through the one biopsy punch opening;
   a tumescent cannula for injecting a tumescent fluid into the body of the patient, wherein the tumescent cannula comprises an attachable garden spray cannula, wherein the tumescent cannula receives the fiber of the laser component, and wherein the tumescent cannula is insertable into the body of the patient through the one biopsy punch opening;
   a nutational infrasonic liposculpture ("NIL") component to remove a fat cell, the NIL component further comprising a source of nutational motion and a source of suction;
   at least one NIL cannula; and
   wherein laser light is transmittable by the fiber into the body of the patient through the one biopsy punch opening to heat the fat cell to induce an at least partial liquefaction of the fat cell;
   wherein the NIL component is attached to the at least one NIL cannula and wherein the at least one NIL cannula is insertable into the body of the patient through the one biopsy punch opening; and
   wherein the fat cell that is at least partially liquefied is removable from the body by suction created by the source of suction through the at least one NIL cannula when the NIL cannula is inserted into the body through the one biopsy punch opening and performing a nutational movement within the body, wherein each of the tumescent cannula, the laser component, and the NIL cannula pass through the same one biopsy punch opening.

2. The system of claim 1, wherein the fiber is at least partially enclosed by the tumescent cannula.

3. The system of claim 1, wherein the NIL component provides the nutational movement to the at least one NIL cannula during removal of the fat cell.

4. The system of claim 1, wherein the NIL component includes an output through which the fat cell is harvestable.

5. The system of claim 4, wherein the fat cell is harvestable from the body from a first location and is implantable into the body at a second location to increase a volume of fat cells adjacent to the second location.

6. The system of claim 5, wherein a stem cell is implantable with the fat cell at the second location to increase a likelihood of acceptance of the fat cell by the body at the second location.

7. The system of claim 1, wherein the one biopsy punch opening has a diameter of less than two millimeters.

8. A method, comprising:
   propelling an anesthetic into a body of a patient at a location using a jet injector;
   creating one biopsy punch opening in the skin of the patient at the location using a biopsy punch;
   inserting a tumescent cannula into the body of the patient through the one biopsy punch opening;
   injecting a tumescent fluid into the body of the patient through the one biopsy punch opening via the inserted tumescent cannula to cause a fat cell in the body to become tumescent and to facilitate at least partial liquefaction of the fat cell, wherein the tumescent cannula comprises an attachable garden spray cannula;
   inserting a fiber of a laser component into the body of the patient through the one biopsy punch opening;
   operating the laser component to transmit laser light into the body of the patient through the one biopsy punch opening via the inserted fiber;
   inserting a NIL cannula attached to a NIL component into the body of the patient through the one biopsy punch opening; and
   extracting the fat cell through the one biopsy punch opening via suction through the NIL cannula attached to the NIL component, while the NIL cannula is inserted into the body through the one biopsy punch opening and performing a nutational movement within the body, wherein each of the tumescent cannula, the fiber of the laser component, and the NIL cannula pass through the same one biopsy punch opening.

9. The method of claim 8, wherein the NIL component provides the nutational movement to the NIL cannula.

10. The method of claim 8, wherein the NIL component includes an output through which the fat cell is harvestable and wherein the method further comprises:
    harvesting the fat cell from a first location within the body of the patient using the output.

11. The method of claim 10, further comprising:
    implanting the fat cell that is harvested into the body at a second location to increase a volume of fat cells adjacent to the second location.

12. The method of claim 11, wherein implanting the fat cell further comprises implanting a stem cell with the fat cell at the second location to increase a likelihood of acceptance of the fat cell by the body at the second location.

13. The method of claim 8, wherein the one biopsy punch opening has a diameter of less than two millimeters.

14. The method of claim 13, wherein the NIL cannula has a diameter that is as between two millimeters and four-and-a-half millimeters.

15. A method, comprising:
    propelling a numbing component into the skin of a patient at a location using a jet injector
    creating one biopsy punch incision at the location using a biopsy punch;
    injecting a tumescent fluid into a body of the patient via a tumescent cannula that extends through the one biopsy punch incision, the tumescent cannula comprising an attachable garden spray cannula;
    inserting an optical fiber into the body of the patient through the one biopsy punch incision at the location; and
    operating a laser to be transmitted through the one biopsy punch incision via the optical fiber to heat a fat cell within the body to induce an at least partial liquefaction of the fat cell; and inserting a NIL cannula that is attached to a NIL component into the body of the patient through the one biopsy punch incision at the location; and extracting the fat cell through the one biopsy punch incision by suction through the NIL cannula that is attached to the NIL component, while the NIL cannula is positioned at least partially within the body, extended through the one biopsy punch incision, and performing a nutational movement within the body, the fat cell being harvestable from the one biopsy punch incision at the location;

wherein causing the fat cell to become tumescent facilitates at least partial liquefaction of the fat cell, and wherein each of the tumescent cannula, the optical fiber, and the NIL cannula pass through the same one biopsy punch incision.

16. The method of claim 15, wherein the one biopsy punch incision created by the biopsy punch does not require stitches so that the method produces a naturally healing, scarless wound at the one biopsy punch incision.

17. The method of claim 15, wherein the one biopsy punch incision has a diameter of less than two millimeters.

* * * * *